United States Patent
Cline et al.

[11] Patent Number: 5,873,845
[45] Date of Patent: Feb. 23, 1999

[54] ULTRASOUND TRANSDUCER WITH FOCUSED ULTRASOUND REFRACTION PLATE

[75] Inventors: Harvey Ellis Cline, Schenectady; Ronald Dean Watkins, Niskayuna; George Raymond Russell, Albany; Kullervo Henrik Hynynen, Medfield, all of N.Y.

[73] Assignee: General Electric Company, Schenectady, N.Y.

[21] Appl. No.: 818,988

[22] Filed: Mar. 17, 1997

[51] Int. Cl.⁶ .................................................. A61B 17/22
[52] U.S. Cl. ................................................. 601/3; 310/334
[58] Field of Search ......................... 601/2–4; 600/439; 310/334, 335

[56] References Cited

U.S. PATENT DOCUMENTS

| | | |
|---|---|---|
| 3,941,456 | 3/1976 | Schilz et al. . |
| 4,331,021 | 5/1982 | Lopez et al. . |
| 4,535,630 | 8/1985 | Samodovitz . |
| 4,865,042 | 9/1989 | Umemura et al. ................. 600/439 |
| 4,893,624 | 1/1990 | Lele ...................................... 601/3 |
| 4,936,303 | 6/1990 | Detwiler et al. ..................... 601/3 |
| 4,949,708 | 8/1990 | Takayama ............................ 601/3 |
| 5,140,860 | 8/1992 | Hüschelrath et al. . |
| 5,247,935 | 9/1993 | Cline et al. . |
| 5,275,165 | 1/1994 | Ettinger et al. . |
| 5,329,930 | 7/1994 | Thomas, III et al. . |
| 5,368,032 | 11/1994 | Cline et al. . |
| 5,371,483 | 12/1994 | Bhardwaj . |
| 5,402,792 | 4/1995 | Kimura ............................. 600/472 |
| 5,427,106 | 6/1995 | Breimesser et al. . |
| 5,443,068 | 8/1995 | Cline et al. . |
| 5,458,120 | 10/1995 | Lorraine . |
| 5,487,306 | 1/1996 | Fortes . |
| 5,490,840 | 2/1996 | Uzgiris et al. . |
| 5,526,814 | 6/1996 | Cline et al. . |

*Primary Examiner*—Brian Casler
*Attorney, Agent, or Firm*—Marvin Snyder; Douglas E. Stoner

[57] ABSTRACT

A system for performing surgery by vibrational heating employs an ultrasonic transducer 80 for focusing a spherical ultrasound wave on a focal region. In one embodiment a refraction plate 410 having a spherical surface facing the transducer and a refracting surface with refracting pyramid elements 450 facing the subject causes the ultrasound beam to impinge on a plurality of overlapping focal regions and thereby expand the focal area of the transducer. In a second embodiment the refraction plate comprises a phased lens 600 having a constant thickness at any angular location but with its thickness varying linearly over $2\pi$ radians or multiples thereof.

13 Claims, 6 Drawing Sheets

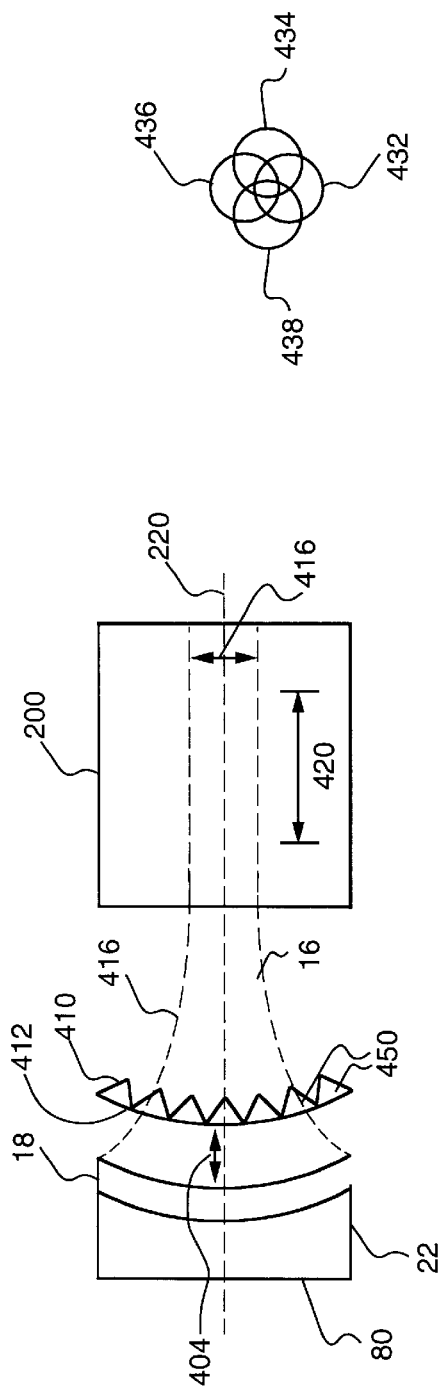
*FIG. 4a*
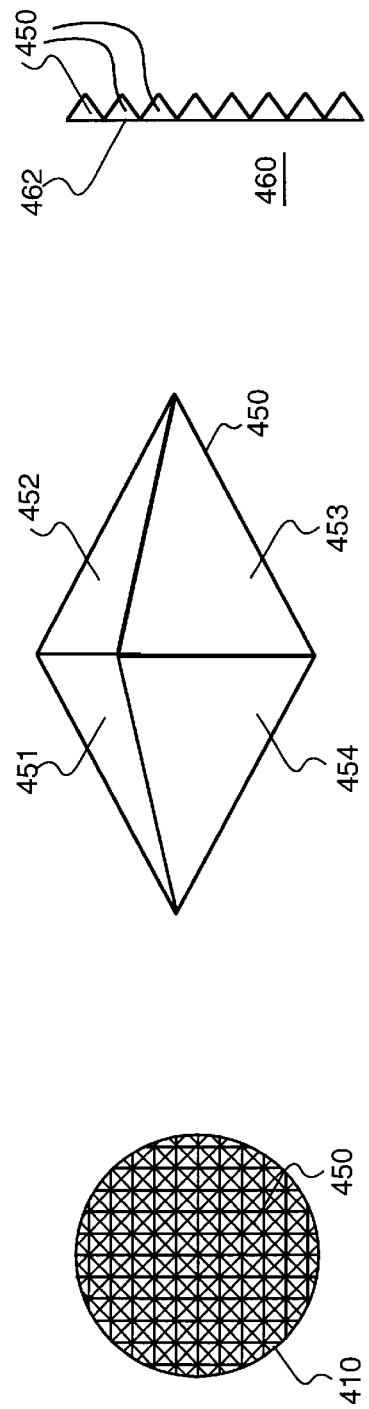
*FIG. 4b*
*FIG. 5a*
*FIG. 5b*
*FIG. 5c*

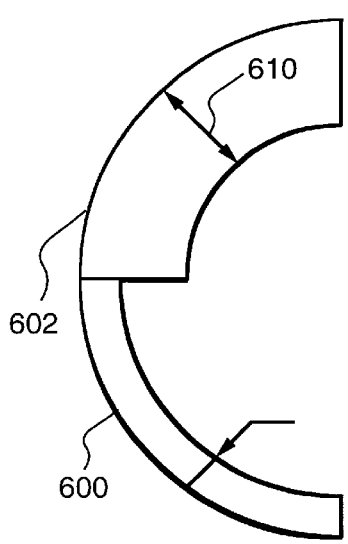 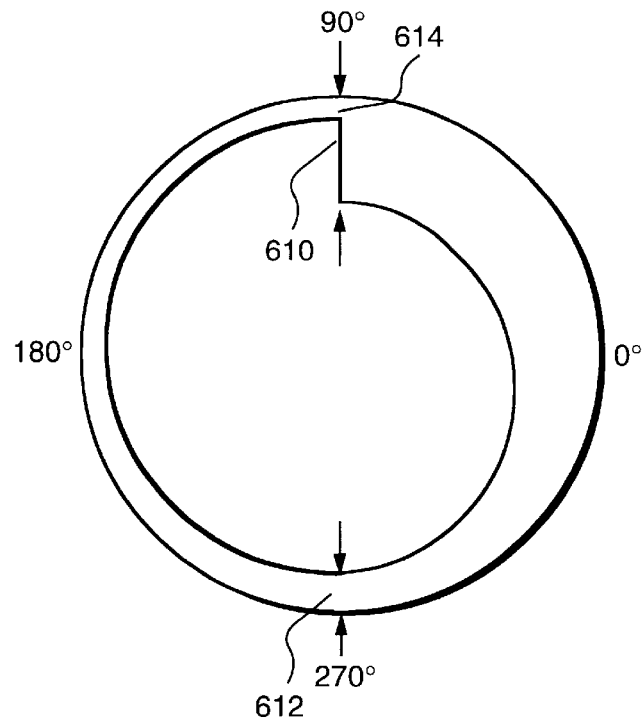
FIG. 6a    FIG. 6b
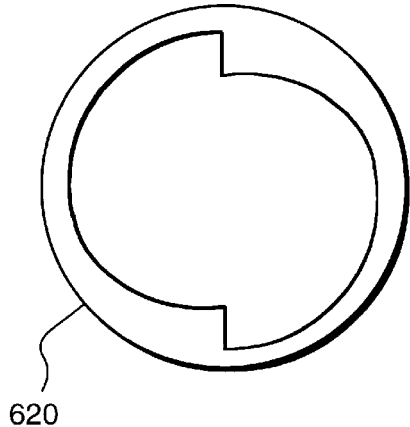 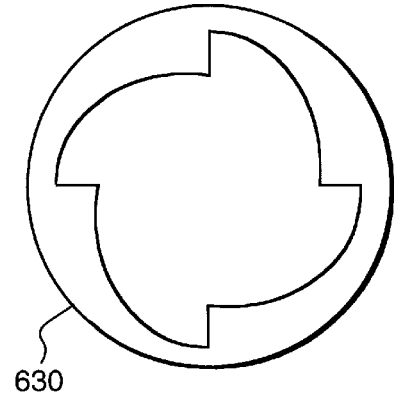
FIG. 9    FIG. 10 max (P) = 1.25•10³ max (P2) = 634.77

5,873,845

ULTRASOUND TRANSDUCER WITH FOCUSED ULTRASOUND REFRACTION PLATE

BACKGROUND OF THE INVENTION

This invention relates to a system for performing surgery by vibrational heating and more particularly to a system for performing surgery with ultrasonic heating guided by magnetic resonance (MR) imaging.

Conventional Magnetic Resonance Imaging (MRI) provides the radiologist with internal views of a subject's anatomy. MRI can produce excellent contrast between different tissues and is useful in planning surgical procedures. A tumor in a subject is much more visible in an MR image than as seen in actual surgery because a tumor and normal tissue often look similar in surgery. The actual tumor may also be obscured by blood during surgery. A view of the heated region is provided with the use of MR temperature sensitive pulse sequences. Known MR temperature sensitive pulse sequences are described, for example, in D. LeBihan et al. U.S. Pat. No. 4,914,608 In-Vivo Method for Determining and Imaging Temperature of an Object/Subject from Diffusion Coefficients Obtained by Nuclear Magnetic Resonance, issued Apr. 3, 1990. Experimentation has shown that a heated zone above a critical temperature destroys living tissue. This zone increases in size with time, as the heat is applied, to reach a steady state of both temperature and heat flow. If the maximum temperature is limited to 100° C., then the heated zone, i.e., the area exceeding a critical temperature causing destruction of tissue, approaches 1 centimeter in diameter. It is difficult to predict the heated zone geometry because the heat flow depends on the perfusion of blood as well as the tissue thermal properties.

Tumors have been selectively destroyed in cancer subjects using focused ultrasound heating in the absence of MR imaging at the University of Arizona, as reported by B. E. Billard et al., "Effects of Physical Parameters on High Temperature Ultrasound Hyperthermia", *Ultrasound in Med. & Biol.* Vol. 16, No. 4, pp. 409–420, 1990 and hereby incorporated by reference. Billard et al. disclose that the control of heat is improved by using short heating pulses where the effect of blood perfusion is negligible. However, since they do not image the temperature distribution, it is difficult to hit small, deep laying targets.

As indicated above, an ultrasound transducer produces a relatively small, intense focal region. Often the focal region of the ultrasound transducer is smaller than the tissue that requires treatment. Accordingly, the focal region must be moved across the morbid tissue to fully ablate the tumor. The focal region is moved by sweeping the treatable area with the focused ultrasound beam. Sweeping can be accomplished by mechanically moving the transducer relative to the patient, or vice versa, but such methods are cumbersome. An alternative method for sweeping the focal region relies upon phased array treatment wherein electronic circuitry drives an array of ultrasound transducers to sweep a phased array ultrasonic beam over the treatment area. However, phased array ultrasound devices are complex and hence expensive to fabricate and to operate.

Accordingly, a need exists for a relatively simple, efficient and economic apparatus for treating a larger volume of tissue without significantly changing the size of the transducer or requiring the complexity of a phased array transducer and phased array driving electronics.

SUMMARY OF THE INVENTION

A refraction plate employed to expand the focal region of an ultrasound beam without the use of a phased array has, in one embodiment, a spherical surface facing an ultrasound transducer and an array of refracting elements, such as pyramids, facing the patient. The refracting elements bend the ultrasound waves to focus them at four overlapping locations, thereby expanding the focal region. In another embodiment, a refraction plate that forms a phased lens with a mode equal to one or more has a spherical surface facing the ultrasound transducer. The surface facing the patient has a thickness that is constant at any angular location and varies linearly by $2\pi$ one or more integral number of times although, as an alternative, the thickness may vary by two or more integral number of times around the circumference of the plate. Sound waves leaving the surface facing the patient are refracted through $2\pi$ radians and create a diffraction pattern at the focus region. The diffraction pattern expands the outer circumference of the focus zone and cancels sound wave energy near the axis of the plate. The phased lens establishes an annular, cylindrical focus region, the outer and inner diameters of which expand with higher order modes.

BRIEF DESCRIPTION OF THE DRAWING

FIG. 4a is a cross sectional diagram of a spherical transducer, showing a refraction plate situated between the transducer and the subject for expanding the focal region;

FIG. 4b illustrates the expanded focal region generated by the refraction plate of FIG. 4a;

FIG. 5a is a plan view of the refraction plate;

FIG. 5b is an expanded perspective view of a refraction element;

FIG. 5c illustrates a planar refraction plate;

FIG. 6a is a sectional view of a phased lens;

FIG. 6b is a plan view of the phased lens of FIG. 6a;

FIG. 9 is a plan view of a mode two phased lens;

FIG. 10 is a plan view of a mode four phased lens;

DETAILED DESCRIPTION OF THE INVENTION

Figure 1:
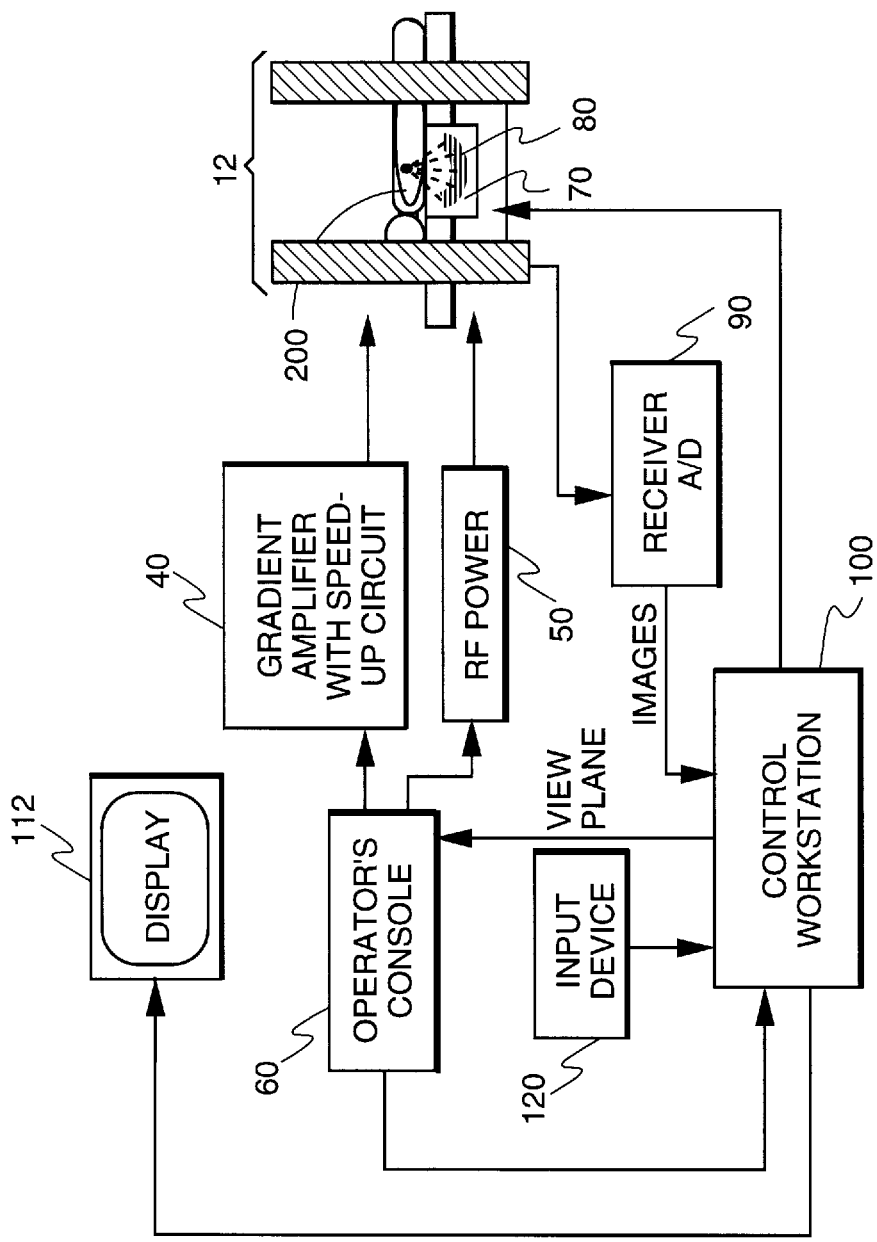
FIG. 1 is a schematic block diagram of a magnetic resonant pulsed heat system according to the present invention.

FIG. 1 illustrates a magnetic resonance imaging system 12 incorporating the invention. The magnetic resonant (MR) imaging system employs pulse sequences in the well known manner to rapidly acquire raw MR data used in constructing images of a subject 200. A gradient amplifier 40 and an rf power source 50 supply the power for the sequences. An operator console 60 is used to control the imaging system. Raw data are sent from a receiver 90 to a control workstation 100 having a screen 112 for displaying images to the operator. Control workstation 100 computes a path to a desired location in subject 200 from an ultrasound transducer 80 in a trajectory which avoids bone and air spaces.

The operator indicates the desired location of the focal point of ultrasound transducer 80 by means of an input device 120 which may be a three-dimensional pointing device such as a trackball or a mouse. Control workstation 100 actuates positioning means 70 to position ultrasound transducer 80. MR imaging system 12 then employs pulse sequences to rapidly acquire temperature sensitive images of the subject 200. Since both internal structures and heated regions are imaged, the operator can accurately position the heated region to correspond to a desired internal structure through input device 120.

Figure 2:
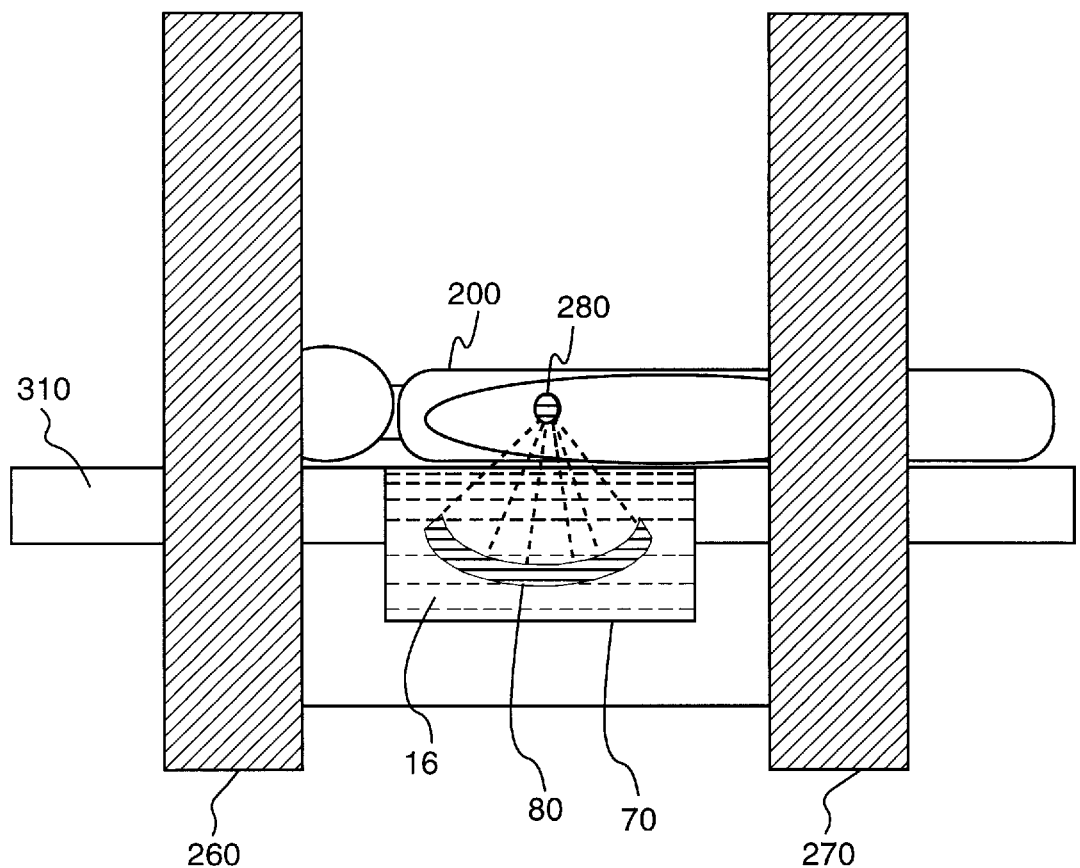
FIG. 2 is a diagrammatic illustration of a subject positioned for surgery within the bore of the magnets of an MRI system of FIG. 1.

As shown in FIG. 2, subject 200 is situated on a table 310 designed to accommodate a focused ultrasound transducer 80 in an ultrasound-conducting liquid 16 chosen to conduct ultrasonic energy with little attenuation. Ultrasound transducer 80 can be moved inside the bore of magnets 260, 270 by positioning means 70 to focus on various locations in subject 200. A path for the ultrasound beam is computed by control workstation 100 (FIG. 1) from a set of images of the subject taken during surgery planning which avoids bone or air. The energy produced by ultrasound transducer 80 is aimed along the computed path by positioning means 70, focused onto a tumor 280 and pulsed to selectively heat the tumor. The ultrasound transducer is moved while the operator views cross-sectional, temperature sensitive images.

Figure 3:
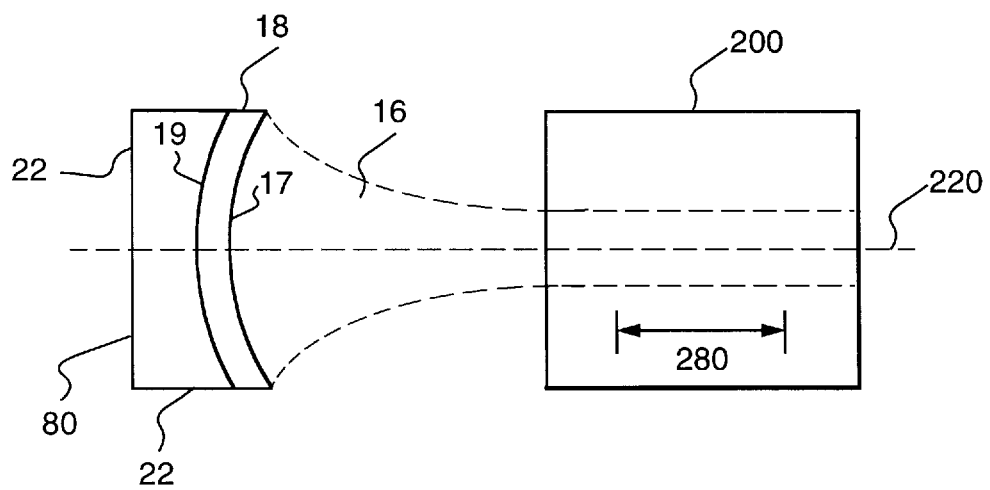
FIG. 3 is a cross sectional diagram of a spherical transducer, showing its adjacent focus region.

A prior art spherical ultrasound transducer 80, shown in FIG. 3, has a spherical concave surface in three dimensions, thus resembling a bowl. Being curved, the transducer focuses sound energy over a tube-shaped region 280. The transducer comprises a curved, piezoelectric element 18 having one electrode 17 on the front side facing subject 200, one electrode 19 on the opposite, rear side, and a backing 22 of matching layers to match the acoustical impedance of transducer 80 to that of coupling medium 16. Medium 16 is water or gel having the same density as water, and interfaces transducer 80 with subject 200. Focal region 280 is a relatively small and concentrated region around an axis 220 passing through the center of spherical transducer 80.

FIG. 4a shows one embodiment of the invention using a spherical refraction plate 410 situated between transducer 80 and subject 200. The space 404 between transducer 80 and refraction plate 410 is approximately equal to the wavelength of sound in medium 16. Where the medium is water and the frequency of sound is 1.5 MHz, space 404 is about 1 millimeter. Refraction plate 410 effectively increases the diameter 416 of focal region 420. Refraction plate 410 has a first, spherical surface 412 facing the spherical surface of transducer 80. The surface of refraction plate 410 facing subject 200 is an array of refracting elements. In the preferred embodiment each refracting element is a pyramid 450 shown in greater detail in FIG. 5b. FIG. 4b illustrates the expanded focal region generated by refraction plate 410 of FIG. 4a.

Refraction plate 410 refracts sound waves as they leave one medium and enter another. When sound waves leave one medium and enter another in which the speed of sound differs, the direction of the waves is altered. The change in direction results from a change in speed of the waves. When sound waves travel slower in the second medium, the waves are refracted toward the normal, i.e. an imaginary line perpendicular to the boundary between the mediums. If sound travels faster in the second medium, the waves will be refracted away from the normal.

In a preferred embodiment, refraction plate 410 is comprised of polystyrene plastic, and so the sound waves travel faster in the plastic of the refraction plate than in the water. Accordingly, the waves are refracted away from the normal and therefore away from axis 220 of transducer 80.

FIG. 5a is a typical planar view of spherical refraction plate 410, which is covered with an array of pyramids 450. Each pyramid comprises a base and has four sides that rise to an apex, thereby defining four surfaces, 451–454, as shown in FIG. 5b. Each surface refracts the spherical sound wave away from axis 220 (FIG. 4a) and toward an alternate focal point. As a result, refraction plate 410 forms four focal regions 432, 434, 436, and 438, as shown in FIG. 4b, around axis 220, effectively expanding the focal area of the transducer. As an alternative embodiment, a refraction plate 460 may be formed as shown in FIG. 5c. There, refraction plate 460 has a planar surface 462 facing the transducer.

The spherical refraction plate may, as another alternative, be mounted directly upon the spherical surface of transducer 80. In the preferred method of operation, transducer 80 generates a sound wave at a frequency of about 1.5 megahertz. The wavelength of sound in water for 1.5 megahertz is approximately one millimeter. Accordingly, spacing 420 is set at about one millimeter. Alternatively, as discussed above, spherical refraction plate 410 may be mounted directly on the spherical surface of transducer 80. A suitable sinusoidal voltage is applied to transducer 80 and spherical sound waves are generated by the transducer. Given the one millimeter spacing and the one millimeter wavelength, the spherical sound waves impinge on spherical surface 412 (FIG. 4a), in phase. However, upon leaving the refraction plate, the waves encounter pyramids 450. Each surface 451–454 of a pyramids deflects waves slightly away from the axis 220 and thus spreads the wave out from original focal region 280. Pyramids 450, in effect, create four focal regions 432, 434, 436, and 438 that are superimposed upon each other to form a new focal region 420 which includes the four regions 432, 434, 436, and 438 as shown in FIG. 4b.

The radii of curvature of transducer 80 and surface 412 of refraction plate 410 are substantially the same, so that the two spherical surfaces are concentric. Refraction plate 410 has a typical diameter of about 10 centimeters and is approximately 3 millimeters thick. The surface of the refraction plate is milled to form an array of pyramids, each with a one centimeter square base and one millimeter of elevation.

In lieu of a four-sided raised pyramid, those skilled in the art will appreciate that other refracting surfaces can be used to spread the focal region of the beam. For example, instead of raised pyramid surfaces, the surfaces could be depressions, so that the apexes of the pyramids are situated in the refracting surface. Likewise, the pyramids could be three-sided pyramids. The pyramid shape is not essential and any suitable wedge or facet configuration could be used to fashion a refraction plate.

FIGS. 6a, 6b illustrate a focused ultrasound phased shell lens 600 that also increases the treatment volume of the transducer. Phased shell lens 600 creates a larger beam in the radial dimension while maintaining the axial dimension of focal region 12 (FIG. 1). This is accomplished by varying the phase at different azimuthal angles across the face of shell lens 600. Shell lens 600 constitutes a lens of constant thickness at any given angle, but the thickness varies linearly with the azimuthal angle. Lens 600, shown in FIG. 6a, 6b, is a mode one lens in which, at about 90° thickness 610 is constant. Likewise, at 270°, thickness 612 is also constant. However, around the circumference of lens 600 the thickness linearly increases with angular displacement. At the completion of a rotation, there is a step discontinuity down from the maximum thickness 610 to a minimum thickness 614. So, in mode one lens 600, the thickness varies with a $2\pi$ variation in phase created by a variation in thickness of the lens about the circumference of the lens.

For a sound wave frequency of about 1.5 Mz, the minimum lens thickness 614 is about one millimeter and the maximum thickness is about 2.5 millimeters. In general, the variable thickness of lens 600 is equal to or greater than the change in wavelength of sound in the lens for the chosen frequency. So, a step or variable thickness of 1.5 mm is equal to or greater than the change in wavelength for a 1.5 Mz frequency sound wave in Plexiglas thermoplastic resin, for example. Those skilled in the art will appreciate that other materials may be used, including, for example, polystyrene. In general it is preferred that the speed of sound be faster in the lens than in the surrounding material, i.e., faster than the speed of sound in water.

Figure 7:
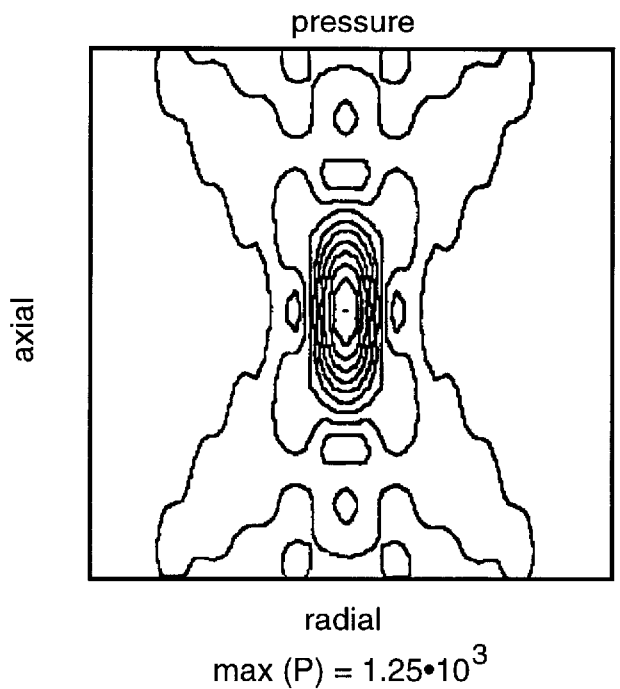
FIG. 7 is a first pressure graph.
Figure 8:
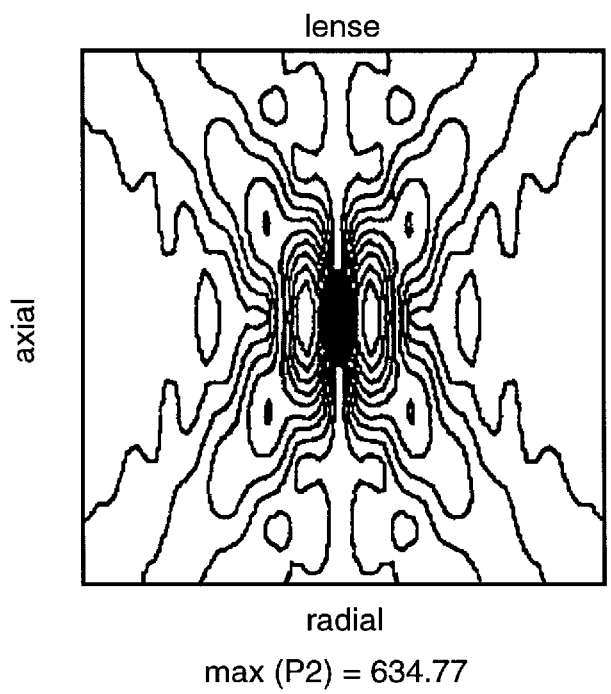
FIG. 8 is a second pressure graph.

Lens 600 will produce pressure magnitudes depending upon Huygen's principle. Wavelets from the transducer are superimposed on spherical surface 602 and propagate through different thicknesses of the lens to create a diffraction pattern. The solution for a wave in cylindrical coordinates at a distance from a lens is give by a Bessel function, JN where N is 0 or a positive integer indicative of the mode. In the examples given below, the Bessel functions $J_0$ and $J_1$ are integrated from the center of the focal regions to the outer periphery of the focal region. If the phase is constant, the pressure from any ring is a zero order Bessel Function. By adding contributions from concentric rings, one can calculate the pressure pattern. In the case of a lens with varying thickness around a ring a Bessel Function of order one is obtained. The contributions from a ring are zero at the axis to create a wider focal spot. Calculated diffraction patterns are shown in FIGS. 7, 8 by superimposing ring contributions for the two cases. The calculation of pressures for the waves shown in FIGS. 7, 8 is given below where:

R=80 mm, radius of curvature of lens 600 a=50 mm, half the diameter of the 100 mm lens k=$2\pi/\lambda$, wave number where X is the wave length at 1.5 Mz i=increments from 0 to 50 of the aperture j=increments 0 to 100 of the axial distance from the focal spot $$r_i = \frac{i-25}{5},$$

where $r_i$ is the radial distance (mm) from the axis of focus $$Z_j = \frac{j-50}{5},$$

where $Z_j$ is the axial length (mm) from the focal axis

The solution for a zero mode lens (FIG. 7) is:

$$P_{0_{i,j}} = \left| \int_0^a \exp\left( \frac{i \cdot k \cdot z_j \cdot \rho^2}{2 \cdot R^2} \right) \cdot J_0\left( \rho \cdot k \cdot \frac{r_i}{R} \right) \cdot \rho d\rho \right|$$

The solution for a mode one lens (FIG. 8) is:

$$P_{1_{i,j}} = \left| \int_0^a \exp\left( \frac{i \cdot k \cdot z_j \cdot \rho^2}{2 \cdot R^2} \right) \cdot J_1\left( \rho \cdot k \cdot \frac{r_i}{R} \right) \cdot \rho d\rho \right|$$

Figure 11A:
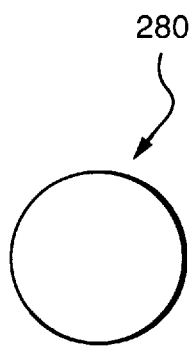
FIGS. 11a, 11b, 11c and 11d are cross sectional diagrams of the focal regions generated by mode zero and the cylindrical, annular focal regions of the mode one, mode two and mode three phased lenses, respectively.
Figure 11B:
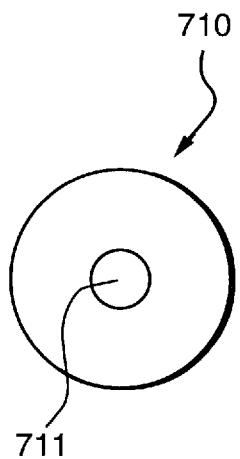
Figure 11C:
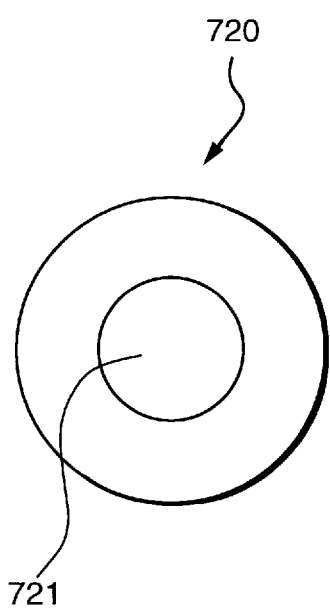
Figure 11D:
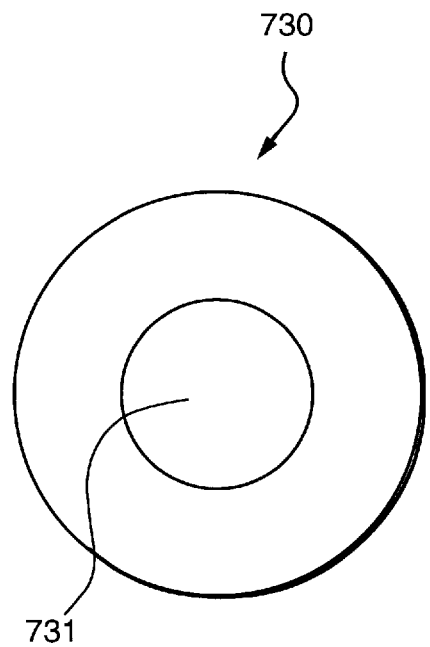

A phased lens may have any integral number order of transmission modes of one or greater. To change the mode of a lens, the variation in thickness around the angular dimensions may be an integral number N of $2\pi$ or the $2\pi$ variation may occur over N sectors to result in a lens that has contributions of an Nth order Bessel Function for each ring. A zero order lens is equivalent to a spherical lens with no variation in thickness. Such a lens will produce a typical focal region 280, as shown in FIG. 11a.

A mode two lens 620 is shown in FIG. 9. Lens 620 has its thickness in the circumferential direction varied twice over $2\pi$ radians. As an alternative, the lens thickness in the circumferential direction can vary twice as much as it varies in FIG. 6; that is, a mode two lens can have its thickness vary in the circumferential direction by twice the linear variation of lens 600. In other words, if thickness of the zero order lens varied in the circumferential direction from a minimum of 1 millimeter to a maximum of about 2.5 millimeters, then thickness of a second order lens would vary in the circumferential direction from a minimum of 1 millimeter to a maximum 4 millimeters. The same principals apply to a mode four lens 630, shown in FIG. 10.

Since the phase varies by $2\pi$ for each mode, the net result is that the diffraction pattern will cancel out sound waves along axis 220 in focal region 420 (FIG. 4a). This creates a hole in the focal region where there is no sonic energy. Likewise, the diffraction pattern expands the outer perimeter of the treatment area.

FIGS. 11a–11d illustrate cross sections of focal regions for lenses from mode zero through mode three, respectively. The central hole and the outer diameter increase as the mode number increases. Thus aperture 721 of the mode two lens focal region is larger than aperture 711 of the mode one lens focal region and likewise aperture 731 of the mode three lens focal region is larger than aperture 721 of the mode two lens focal region. Thus the mode one and higher order lenses generate cylindrical, annular focal regions where the outer and inner diameters increase with increasing mode numbers.

In a preferred embodiment, lens 600 comprises a 10 centimeter diameter spherical plate with an 8 centimeter radius that is milled to have a variable thickness around the angular coordinate while having a constant thickness in the radial direction at any angular location. Lens 600 may be placed on a 10 centimeter diameter spherical shell ultrasound transducer and thus create a larger ultrasound beam. Lens 600, shown in FIG. 3, may be mounted on the spherical surface of transducer 18 and spaced from the transducer by a wavelength of sound in medium 16.

While only certain preferred features of the invention have been illustrated and described, many modifications and changes will occur to those skilled in the art. It is, therefore, to be understood that the appended claims are intended to cover all such modifications and changes as fall within the true spirit of the invention.

We claim:

1. A system for vibrational heating of tissue with ultrasonic energy, comprising:

a spherical ultrasound transducer having a spherical surface for generating a spherical wave of ultrasonic energy in a direction toward a single focal region; and a refraction plate disposed between the spherical ultrasound transducer and the focal region for refracting said spherical wave of ultrasonic energy to a plurality of refraction focal regions, said refraction plate comprising a phased lens having a first surface facing the spherical ultrasound transducer and being substantially concentric with the spherical surface of the transducer, a center substantially axially aligned with the center of the spherical surface of the transducer, an outer diameter substantially equal to the outer diameter of the spherical transducer, and a second surface facing the focal region, said phased lens having a mode of transmission equal to an integral number of one or greater.

2. The system of claim 1 wherein the thickness of the phased lens varies with azimuthal angle by an integral number of $2\pi$.

3. A system for vibrational heating of tissue with ultrasonic energy, comprising:

a spherical ultrasound transducer having a spherical surface for generating a spherical wave of ultrasonic energy in a direction toward a single focal region; and a refraction plate disposed between the spherical ultrasound transducer and the focal region for refracting said spherical wave of ultrasonic energy to a plurality of refraction focal regions, said refraction plate comprising an array of refracting elements in the shape of four sided pyramids for refracting the spherical wave of ultrasonic energy and generating four refraction focal regions.

4. The system of claim 3 wherein the refraction plate comprises a circular body of a material selected from the group consisting of Plexiglas thermoplastic resin and polystyrene.

5. The system of claim 3 wherein one side of the base of each of the pyramids has a length about ten times the height of said each of the pyramids, respectively.

6. A system for vibrational heating of tissue with ultrasonic energy, comprising:

a spherical ultrasound transducer having a spherical surface for generating a spherical wave of ultrasonic energy in a direction toward a single focal region; and a refraction plate disposed between the spherical ultrasound transducer and the focal region for refracting said spherical wave of ultrasonic energy to a plurality of refraction focal regions, said spherical ultrasound transducer having a spherical surface of a first radius of curvature and said refraction plate having a first surface facing the transducer and a second surface facing the focal region and comprising a plurality of refracting surfaces in the form of an array of four-sided pyramid shapes with the apex of each of said pyramids pointing away from the second surface.

7. The system of claim 6 wherein the first surface of the refraction plate comprises a spherical surface of substantially the same radius of curvature as, and concentric with, the spherical surface of the transducer.

8. The system of claim 7 wherein the concentric refraction plate is mounted on the spherical surface of the transducer.

9. The system of claim 6 wherein the ultrasound transducer is adapted to emit vibrational energy of a predetermined wavelength and the refraction plate is spaced by said wavelength from the spherical surface of the transducer.

10. The system of claim 6 wherein the first surface of the refraction plate is substantially planar.

11. A system for vibrational heating of tissue with ultrasonic energy, comprising:

a spherical ultrasound transducer having a spherical surface for generating a spherical wave of ultrasonic energy in a direction toward a single focal region; and a refraction plate disposed between the spherical ultrasound transducer and the focal region for refracting said spherical wave of ultrasonic energy to a plurality of refraction focal regions, said refraction plate comprising a phased lens having a first surface facing the spherical ultrasound transducer and being substantially concentric with the spherical surface of the transducer, a center substantially axially aligned with the center of the spherical surface of the transducer, an outer diameter substantially equal to the outer diameter of the spherical transducer, and a second surface facing the focal region, the phased lens having a thickness along any radius from the center to the edge that is constant and varies with angular location.

12. The system of claim 11 wherein the thickness of the phased lens along any radius from the center to the edge is constant and the thickness varies linearly with angular location.

13. The system of claim 12 wherein the thickness of the phased lens is determined by the wavelength of the frequency of ultrasonic energy in the phased lens.

* * * * *